United States Patent
Biondo et al.

(10) Patent No.: US 10,507,844 B2
(45) Date of Patent: Dec. 17, 2019

(54) DRIVE-CYCLE SAMPLING AND MONITORING FOR IMPAIRMENT DETECTION SYSTEM

(71) Applicant: GM GLOBAL TECHNOLOGY OPERATIONS LLC, Detroit, MI (US)

(72) Inventors: William A. Biondo, Beverly Hills, MI (US); David T. Proefke, Troy, MI (US); Fred W. Huntzicker, Ann Arbor, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 93 days.

(21) Appl. No.: 15/715,567

(22) Filed: Sep. 26, 2017

(65) Prior Publication Data

US 2019/0092342 A1 Mar. 28, 2019

(51) Int. Cl.
| | |
|---|---|
| *A61B 5/00* | (2006.01) |
| *B60W 50/12* | (2012.01) |
| *A61B 5/18* | (2006.01) |
| *B60W 10/04* | (2006.01) |
| *B60W 10/20* | (2006.01) |

(Continued)

(52) U.S. Cl.
CPC .............. *B60W 50/12* (2013.01); *A61B 5/18* (2013.01); *A61B 5/4845* (2013.01); *A61B 5/6893* (2013.01); *A61B 5/742* (2013.01); *A61B 5/7405* (2013.01); *A61B 5/746* (2013.01); *A61B 5/747* (2013.01); *B60W 10/04* (2013.01); *B60W 10/20* (2013.01); *B60W 10/30* (2013.01); *B60W 30/12* (2013.01); *B60W 30/14* (2013.01); *G05D 1/0061* (2013.01); *G08B 25/10* (2013.01); *B60W 2540/24* (2013.01); *G05D 2201/0213* (2013.01)

(58) Field of Classification Search
None
See application file for complete search history.

(56) References Cited

U.S. PATENT DOCUMENTS

| | | |
|---|---|---|
| 4,738,333 A | 4/1988 | Collier et al. |
| 8,196,694 B2 | 6/2012 | Biondo et al. |

(Continued)

OTHER PUBLICATIONS

U.S. Appl. No. 15/229,625, filed Aug. 5, 2016, Biondo et al.
U.S. Appl. No. 15/603,809, filed May 24, 2017, Biondo et al.
U.S. Appl. No. 15/715,567, filed Sep. 26, 2017, Biondo et al.

*Primary Examiner* — Tamara L Weber

(57) ABSTRACT

A system includes an impairment sample module, impairment value calculator module, threshold comparison module, warning alert module, and intervention module. The impairment sample module may be configured to obtain a first impairment sample for an operator of a vehicle while the vehicle is running. The impairment value calculator module may be configured to calculate a first impairment value based on the first impairment sample. The threshold comparison module may be configured to compare the first impairment value to a first threshold value corresponding to a first range of impairment and a second threshold value corresponding to a second range of impairment. The warning alert module may be configured to generate a warning alert in response to determining that the first impairment value exceeds the first threshold value. The intervention module may be configured to execute driver intervention protocol if the first impairment value exceeds the second threshold value.

22 Claims, 4 Drawing Sheets

(51) Int. Cl.
*B60W 10/30* (2006.01)
*B60W 30/12* (2006.01)
*B60W 30/14* (2006.01)
*G05D 1/00* (2006.01)
*G08B 25/10* (2006.01)

(56) References Cited

U.S. PATENT DOCUMENTS

| | | |
|---|---|---|
| 9,975,552 B2 | 5/2018 | Biondo et al. |
| 2005/0030184 A1* | 2/2005 | Victor .................... B60K 28/06 340/576 |
| 2008/0252466 A1* | 10/2008 | Yopp .................... B60K 28/066 340/576 |
| 2010/0012417 A1* | 1/2010 | Walter ................. B60K 28/063 180/272 |
| 2011/0193708 A1* | 8/2011 | Comeau ............... B60K 28/063 340/576 |
| 2017/0101007 A1* | 4/2017 | DeVries ................. H04W 4/80 |
| 2017/0131261 A1 | 5/2017 | Biondo et al. |

* cited by examiner

DRIVE-CYCLE SAMPLING AND MONITORING FOR IMPAIRMENT DETECTION SYSTEM

INTRODUCTION

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

The present disclosure relates to vehicle control systems and methods and more particularly to impairment monitoring and vehicle control systems and methods.

Some vehicles may include an ignition interlock device (IID). For example, installation and use of an IID may be required as a condition for allowing a driver to drive a vehicle. An example type of IID is a breath alcohol ignition interlock device (BAIID).

When a driver attempts to start a vehicle, the driver inputs a breath sample into the BAIID by blowing air into the BAIID. The BAIID determines a blood alcohol concentration (BAC) of the driver based on concentrations of one or more chemicals (e.g., ethanol) in the air blown into the BAUD. When the breath sample satisfies one or more predetermined criteria (e.g., at least a predetermined volume of air, BAC less than a predetermined value, etc.), the BAIID may allow the driver to start and drive the vehicle. When the one or more of the predetermined criteria are not satisfied, however, the BAIID prevents startup and driving of the vehicle.

Other types of IIDs measure concentration of other types of chemicals in blood of users, such as marijuana, methamphetamines, cocaine, etc., and may utilize different mechanisms, such as touch-based detectors. Like BAIIDs, other types of IIDs prevent startup and driving of the vehicle when one or more predetermined criteria are not satisfied.

SUMMARY

According to a feature, a system for drive-cycle sampling and monitoring for impairment detection is provided. The system may include an impairment sample module, an impairment value calculator module, a threshold comparison module, a warning alert module, and an intervention module. The impairment sample module may be configured to obtain a first impairment sample for an operator of a vehicle while the vehicle is running. The impairment value calculator module may be configured to calculate a first impairment value based on the first impairment sample. The threshold comparison module may be configured to compare the first impairment value to a first threshold value corresponding to a first range of impairment and a second threshold value corresponding to a second range of impairment. The second range of impairment may be greater than the first range of impairment. The warning alert module may be configured to generate a warning alert in response to determining that the first impairment value exceeds the first threshold value. Finally, the intervention module may be configured to execute driver intervention protocol in response to determining that the the first impairment value exceeds the second threshold value.

In a feature, the intervention module may be further configured to generate an intervention alert and/or control the operation of the vehicle. In one example of the foregoing feature, the intervention alert may include at least one of a driver warning alert and/or a notice of pending vehicle intervention. In another example of the foregoing feature, the intervention module may be further configured to control the operation of the vehicle through at least one of: (i) wait for an intervention delay to expire; (ii) adjust a steering response of the vehicle; (iii) adjust a speed of the vehicle; and/or (iv) adjust an acceleration of the vehicle. In yet another example of the foregoing feature, the intervention module may be configured to control operation of the vehicle by enabling at least one of traction control, stability control, lane keep assist, and/or full-range adaptive cruise control.

In still another example of the foregoing feature the system includes a cellular transceiver that may be configured to determine if cellular coverage is present. In one example of the foregoing feature, the intervention module may be configured to notify emergency services if cellular coverage is present and/or activate a plurality of visual and audible annunciators including at least one of hazard flashers, high-beam headlights, and a horn if cellular coverage is not present. In another example of the foregoing feature, the intervention module may be further configured to (i) determine if a full vehicle stop is appropriate in response to the presence of cellular coverage; (ii) stop the vehicle if the full vehicle stop is appropriate; and/or (iii) set speed limits for the vehicle and activate at least one of the plurality of visual and audible annunciators if the full vehicle stop is not appropriate.

In one feature, the warning alert module of the system may be configured to perform at least one of the following: (i) generate an advisory alert and/or (ii) activate visual annunciators, including at least one of hazard flashers and high-beam headlights.

In another feature, the system may also include an output control module. The output control module may be configured to transmit control signals to at least one of a speaker, a horn, a display, and external lights.

In a feature, the impairment sample module may be configured to obtain a second impairment sample for the operator of the vehicle while the vehicle is running. In another example of this feature, the impairment value calculator module may be configured to calculate a second impairment value based on the second impairment sample. In yet another example of this feature, the threshold comparison module may be configured to compare the second impairment value to the first threshold value corresponding to the first range of impairment and the second threshold value corresponding to the second range of impairment. The second range of impairment may be greater than the first range of impairment. In still another example of this feature, the warning alert module may be configured to generate a warning alert in response to determining that the second impairment value exceeds the first threshold value. In another example of this feature, the intervention module may be configured to execute driver intervention protocol in response to determining that the second impairment value exceeds the second threshold value.

In another example of the foregoing feature, the system may also include a resample calculator module. The resample calculator module may be configured to obtain the second impairment sample a predetermined period of time after obtaining the first impairment sample. The predetermined period of time may be based on the first impairment value.

In one feature, a method for drive-cycle sampling and monitoring for operator impairment is provided. The method may include obtaining a first impairment sample for an operator of a vehicle while the vehicle is running. A first impairment value may be calculated based on the first impairment sample. The first impairment value may be compared to: (i) a first threshold value corresponding to a first range of impairment and (ii) a second threshold value corresponding to a second range of impairment. The second range of impairment may be greater than the first range of impairment. Further, in response to determining that the first impairment value exceeds the second threshold value, a driver intervention protocol may be executed.

In a feature, executing the driver intervention protocol may include at least one of generating an intervention alert and controlling operation of the vehicle. In one example of the foregoing feature, generating an intervention alert may include at least one of generating a driver warning alert and generating a notice of pending vehicle intervention. In another example of the foregoing feature, controlling operation of the vehicle may include at least one of: (i) waiting for an intervention delay to expire; (ii) adjusting a steering response of the vehicle; (iii) adjusting a speed of the vehicle; (iv) adjusting an acceleration of the vehicle; and/or (v) enabling at least one of traction control, stability control, lane keep assist, and full-range adaptive cruise control.

In another example of the foregoing feature, controlling the operation of the vehicle may further include: (i) determining if cellular coverage is present; (ii) if cellular coverage is present, notifying emergency services; and (iii) if cellular coverage is not present, activating a plurality of visual and audible annunciators including at least one of activating hazard flashers, flashing high-beam headlights, and honking vehicle horn. In one example of the foregoing feature, the method may also include, in response to determining the presence of cellular coverage: (i) determining if a full vehicle stop is appropriate; (ii) if the full vehicle stop is appropriate, stopping the vehicle; and (iii) if the full vehicle stop is not appropriate, setting speed limits for the vehicle and activating at least one of the plurality of visual and audible annunciators.

In a feature, the step of generating a warning alert may include at least one of generating an advisory alert and activating visual annunciators, including at least one of hazard flashers and high-beam headlights.

In one feature, the method may include additional steps. For example, the method may include obtaining a second impairment sample for the operator of the vehicle, while the vehicle is running, a predetermined period of time after obtaining the first impairment sample. The predetermined period of time may be based on the first impairment value. A second impairment value may be calculated based on the second impairment sample. The second impairment value may be compared to (i) the first threshold value corresponding to the first range of impairment and (ii) the second threshold value corresponding to the second range of impairment. The second range of impairment may be greater than the first range of impairment. In response to determining that the second impairment value exceeds the first threshold value, a warning alert may be generated. In response to determining that the second impairment value exceeds the second threshold value, the driver intervention protocol may be executed.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

An ignition interlock device (IID) of a vehicle, such as a breath alcohol ignition interlock device (BAIID), prevents the vehicle from moving when the IID measures a concentration of a chemical (e.g., alcohol) in the driver is greater than a predetermined concentration. IIDs may also prevent startup of the vehicle when the concentration is greater than the predetermined concentration. Generally, IIDs do not monitor impairment levels during operation of the vehicle.

The present disclosure includes a system configured to monitor impairment levels of an operator of a vehicle and execute intervention procedures when impairment levels exceed first and second specified threshold levels. The first and second threshold levels correspond, respectively, to (i) a lower warning level and (ii) a higher operational intervention level. Starting with the ignition of the vehicle, an impairment sample may be obtained from of the operator and compared to each of the first and second threshold values. If the higher operational intervention threshold is exceeded, steps may be taken to adjust or restrict operation of the vehicle. If the lower warning threshold is exceeded, action may be taken to alert the operator and/or others in proximity to the vehicle. According to certain examples, the impairment monitoring system set forth herein may be used for impairment monitoring throughout the operation of a vehicle in a minimally intrusive manner, and it may be configured to offer varying responses depending on a level of impairment of the operator. This may allow it to be incorporated as a standard feature in vehicles.

In one example, the impairment system described herein may obtain impairment samples from any number of impairment detection devices and compare the value(s) from the obtained samples with the first and second threshold levels. In some examples, the monitoring system may initialize upon ignition of the vehicle and perform monitoring and/or control functions until either the ignition is cycled off, or the impairment value surpasses the intervention threshold. A sampling frequency for the system may be determined based on the previous impairment value or values. If an impairment value exceeds an operational intervention threshold, steps may be taken (i) to enable safety features present in the vehicle and/or (ii) stop the vehicle when prudent.

Figure 1:
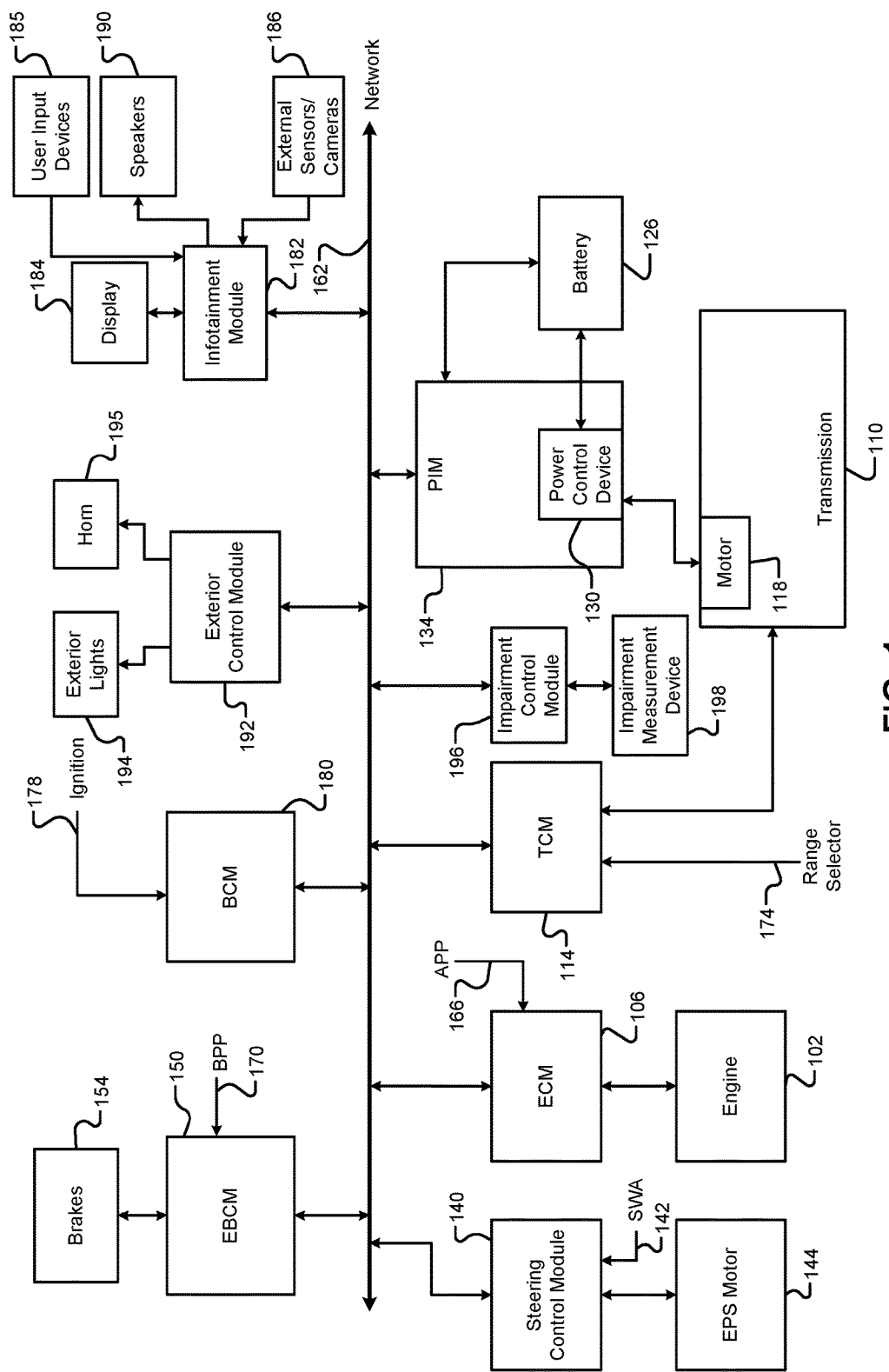
FIG. 1 is a functional block diagram of an example vehicle system.

Referring now to FIG. 1, a functional block diagram of an example vehicle system is presented. While a vehicle system for a hybrid vehicle is shown and will be described, the present disclosure is also applicable to non-hybrid vehicles, electric vehicles, fuel cell vehicles, autonomous vehicles, and other types of vehicles. Also, while the example of a vehicle is provided, the present application is also applicable to non-vehicle implementations.

An engine 102 combusts an air/fuel mixture to generate drive torque. An engine control module (ECM) 106 controls the engine 102. For example, the ECM 106 may control actuation of engine actuators, such as a throttle valve, one or more spark plugs, one or more fuel injectors, valve actuators, camshaft phasers, an exhaust gas recirculation (EGR) valve, one or more boost devices, and other suitable engine actuators.

The engine 102 may output torque to a transmission 110. A transmission control module (TCM) 114 controls operation of the transmission 110. For example, the TCM 114 may control gear selection within the transmission 110 and one or more torque transfer devices (e.g., a torque converter, one or more clutches, etc.).

The vehicle system may include one or more electric motors. For example, an electric motor 118 may be implemented within the transmission 110 as shown in the example of FIG. 1. An electric motor can act as either a generator or as a motor at a given time. When acting as a generator, an electric motor converts mechanical energy into electrical energy. The electrical energy can be, for example, used to charge a battery 126 via a power control device (PCD) 130, such as an inverter. When acting as a motor, an electric motor generates torque that may be used, for example, to supplement or replace torque output by the engine 102. While the example of one electric motor is provided, the vehicle may include zero or more than one electric motor.

A power inverter control module (PIM) 134 may control the electric motor 118 and the PCD 130. The PCD 130 applies (e.g., direct current) power from the battery 126 to the (e.g., alternating current) electric motor 118 based on signals from the PIM 134, and the PCD 130 provides power output by the electric motor 118, for example, to the battery 126. The PIM 134 may be referred to as a power inverter module (PIM) in various implementations.

A steering control module 140 controls steering/turning of wheels of the vehicle, for example, based on driver turning of a steering wheel within the vehicle and/or steering commands from one or more vehicle control modules. A steering wheel angle sensor monitors rotational position of the steering wheel and generates a steering wheel angle (SWA) 142 based on the position of the steering wheel. As an example, the steering control module 140 may control vehicle steering via an electronic power steering (EPS) motor 144 based on information from the SWA 142. However, the vehicle may include another type of steering system.

An electronic brake control module (EBCM) 150 may selectively control mechanical brakes 154 of the vehicle. Modules of the vehicle may share parameters via a controller area network (CAN) 162. The CAN 162 may also be referred to as a car area network. For example, the CAN 162 may include one or more data buses. Various parameters may be made available by a given control module to other control modules via the CAN 162.

The driver inputs may include, for example, an accelerator pedal position (APP) 166 which may be provided to the ECM 106. A brake pedal position (BPP) 170 may be provided to the EBCM 150. The ECM 106 controls actuation of the engine actuators based on the APP 166, the BPP 170, and/or one or more other parameters.

The TCM 114 controls gear selection within the transmission 110, for example, based on a range selector input 174 from a range selector, such as a park, reverse, neutral, drive lever (PRNDL) or another suitable type of transmission range selector. The range selector input 174 may be provided to the TCM 114.

An ignition state 178 may be provided to a body control module (BCM) 180. For example, the ignition state 178 may be generated based on input by a driver via an ignition key, button, or switch. At a given time, the ignition state 178 may be one of off, accessory, run, and crank. When the ignition state 178 transitions from off or accessory to crank, the body control module 180 generally closes a starter switch (e.g., relay). Closing of the starter switch engages a starter with the engine 102 and drives rotation of the starter. When the starter is engaged with the engine 102, rotation of the starter drives rotation of the engine 102 for starting of the engine 102.

The vehicle system may also include an infotainment module 182. The infotainment module 182 controls what is displayed on a display 184 located within a passenger cabin of the vehicle. The display 184 may be a touchscreen display in various implementations and transmit signals indicative of user input to the display 184 to the infotainment module 182. The infotainment module 182 may additionally or alternatively receive signals indicative of user input from one or more other user input devices 185, such as one or more switches, buttons, knobs, etc. located within a passenger compartment of the vehicle.

The infotainment module 182 may receive input from a plurality of external sensors and cameras, generally illustrated in FIG. 1 by 186. For example, the infotainment module 182 may display video, various views, and/or alerts on the display 184 via input from the external sensors and cameras 186. The infotainment module 182 may also generate output via one or more other devices. For example, the infotainment module 182 may output sound via one or more speakers 190 of the vehicle.

The vehicle may also include an exterior control module 192 that controls illumination of various exterior lights of the vehicle. For example, the exterior control module 192 controls illumination of reverse lights, brake lights, headlights, turn lights, hazard lights, and other exterior lights ("exterior lights") 194 of the vehicle. The exterior control module 192 also controls one or more horns, such as horn 195 of the vehicle.

The vehicle also includes an impairment control module 196 and at least one impairment measurement device 198. For example only, the impairment measurement device 198 may include a breath alcohol concentration measurement device (e.g., a breathalyzer) that measures blood alcohol concentration (BAC) based on one or more amounts of one or more chemicals (e.g., ethanol) present in a breath sample input to the device.

While the example of the impairment measurement device 198 including a BAC measurement device will be discussed, the impairment measurement device 198 may include other suitable types of impairment measurement devices and may not be breath-based. For example, the impairment measurement device 198 may measure a concentration of one or more other types of chemicals in blood, such as marijuana (e.g., THC), amphetamines, etc. Other types of impairment measurement devices may be vision-based, such as based on capillary action of a driver's skin in response to the impairment measurement device 198 applying a predetermined type of light (e.g., infrared or laser) to the driver's skin. Still other types of impairment measurement devices may monitor brain activity using an electroencephalogram (EEG). Impairment may be detected, for example, based on an operator's brain waves constituting a pattern associated with intoxication and/or impairment. Measurements provided by another type of impairment measurement device may be used in place of, or in addition to, BAC.

Additionally, the impairment measurement device 198 may incorporate a plurality of impairment measurement devices. Collecting measurements from multiple devices utilizing different methods may reduce false readings. The impairment devices may collect impairment samples in active or passive methods. An advantage of incorporating passive measurement devices may be that the measurements can be recorded during operation of the vehicle with no distraction to the driver. For example, the driver's breath may be monitored passively by using a suction device to collect a breath sample as the driver exhales during routine operation of the vehicle.

While the following examples discuss assessing impairment with regard to BAC, those having ordinary skill will appreciated that the following techniques may apply equally to non-BAC impairment detection methods.

The impairment measurement device 198 may measure a BAC each time a driver requests the starting of the engine 102 (e.g., each time and ignition key, button, or switch is operated). Alternatively, the impairment measurement device 198 may measure a BAC each time the ignition state 178 transitions to one or more of the "on" power modes (e.g., accessory, run, and/or crank). In addition, the impairment measurement device 198 may periodically measure a BAC during operation of the vehicle. This enables appropriate responses even if the impairment value changes during operation, as could be the case if the driver drinks alcohol while driving or shortly prior to driving the vehicle. The time between measurements, or a sample frequency, may be determined by the impairment control module 196.

The impairment control module 196, among other things, generates commands to allow, restrict, or prevent vehicle movement based on the measurements from the impairment measurement device 198. For example, the impairment control module 196 may prevent or stop vehicle movement when the impairment measurement device 198 measures a BAC of greater than the operational threshold value (e.g., 0.08, 0.02, 0.00, or another suitable value). This may be achieved by prohibiting the vehicle from initially shifting the transmission out of park, or if the impairment value was measured during operation, bringing the vehicle to a stop. Additionally, the impairment control module may issue a warning alert to notify the driver when the impairment measurement device 198 measures a BAC of greater than the warning threshold value (e.g., 0.05, 0.01, 0.00, or another suitable value).

For example, the impairment control module 196 may send a warning message to the driver if the BAC is greater than the warning threshold value. This message may serve to inform the driver that an impairment level has been detected and advise against continued operation of the vehicle. This information may be displayed via the display 184 and may be accompanied by an audible note to draw attention to the message. Additionally, the exterior control module 192 may be commanded to activate exterior lighting to indicate to nearby drivers that extra caution may be justified.

Similarly, the impairment control module 196 may command the TCM 114 to maintain the transmission 110 in park and to ignore the range selector input 174 from the range selector when the impairment measurement device 198 measures a BAC of greater than the operational threshold value at the beginning of operation or once stopped. The impairment control module 196, however, may allow the engine 102 to be started despite the BAC being greater than the operational threshold value, for example, to allow an HVAC system of the vehicle to be used to warm and/or cool the passenger compartment of the vehicle.

Under some circumstances, a driver of the vehicle may still wish to drive the vehicle while the driver has a BAC that is greater than the operational intervention threshold value. According to the present disclosure, the impairment control module 196 may consider multiple parameters when determining whether to initiate a full stop of the vehicle when a BAC is greater than the operational threshold value. These parameters may include at least one of a presence of cellular coverage, location of the vehicle, and conditions of a road.

The vehicle may include one or more additional control modules that are not shown, such as a chassis control module, a battery pack control module, etc. The vehicle may omit one or more of the control modules shown and discussed. Additionally, while various modules are shown as separate, one or more modules may be combined.

Figure 2:
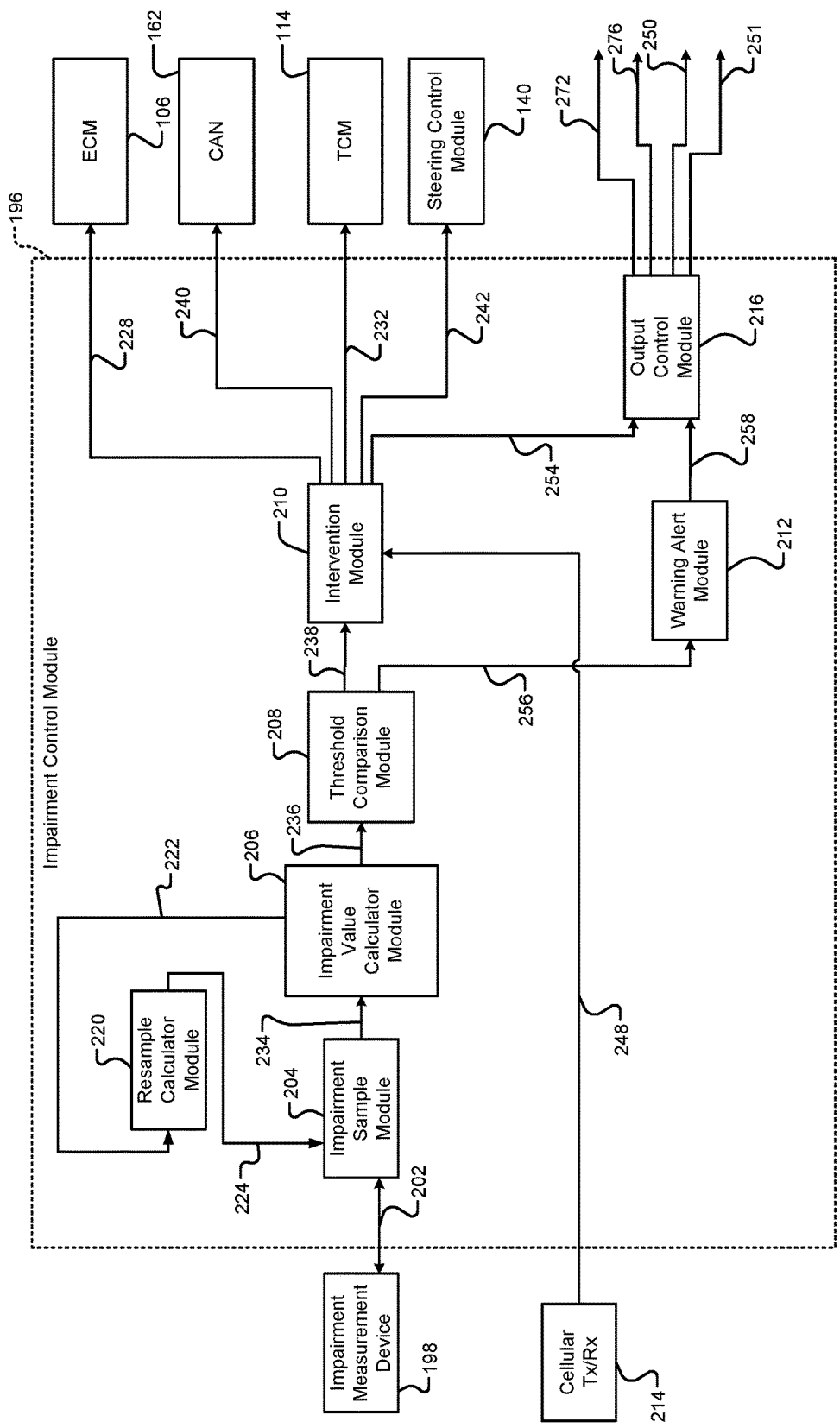
FIG. 2 is a functional block diagram of an example impairment control module.

Referring now to FIG. 2, a functional block diagram of an example implementation of the impairment control module 196 is presented. The impairment control module 196 includes an impairment sample module 204, an impairment value calculator module 206, a threshold comparison module 208, an intervention module 210, a warning alert module 212, an output control module 216, and a resample calculator module 220.

The impairment sample module 204 obtains an impairment sample 202 from the impairment measurement device 198. In this embodiment, the impairment sample 202 corresponds to a BAC, but this may be any number of impairment measurements.

The impairment value calculator module 206 receives the impairment sample 234 from the impairment sample module 204 and calculates an impairment value from the sample. In some embodiments, the impairment measurement devices 198 may provide a sample that contains the impairment value, such as the case when a breathalyzer is used, and the sample is a BAC. However, some impairment measurement devices may not be configured to provide this value.

The threshold comparison module 208 obtains the impairment value signal 236 and compares it with the two threshold values, a first threshold corresponds to the lower warning threshold and a second threshold corresponding to the higher operational intervention threshold. When the impairment value is greater than the warning threshold but less than the operational intervention threshold, the threshold comparison module 208 sends impairment warning information 256 to the warning alert module 212. When the impairment value is greater than the operational intervention threshold, the threshold comparison module 208 sends impairment intervention information 238 to the intervention module 210.

The warning alert module 212 generates a warning alert when the impairment value is greater than the warning threshold value. This alert 258 may be transmitted to the driver by the output control module 216. For example, the warning alert may include a message displayed on a display 184, and an audible note played by speakers 190 to draw attention to the alert. The message may contain information such as the impairment value that was detected and a message advising the driver to stop operation of the vehicle. Additionally, the warning alert module 212 may trigger audible and/or visual output. These outputs may be activated by the output control module 216. For example, the output control module 216 may illuminate or flash (on and off) exterior lights 194 using the control signal 250. These exterior lights 194 may include the high-beam headlights or the hazard lights. The output control module 216 may additionally or alternatively generate sound by sending a control signal 251 for the horn 195. In various implementations, the output control module 224 may command the exterior control module 192 to perform these actions.

The intervention module 210 executes driver intervention protocol when the impairment value is greater than the operational intervention threshold. The degree of driver intervention may vary depending on parameters such as the state of the vehicle and the connection to a cellular network.

Driver intervention protocol may be initiated by the intervention module 210 by setting an intervention delay and sending a notification to the driver of the pending intervention. Additionally, intervention protocol may also include sending a driver warning alert to notify the driver of the impairment level and advise against any further operation of the vehicle. The intervention delay corresponds to a period of time in which the driver may stop using the vehicle by their own means. This may allow the driver to find an adequate location to park or stop the vehicle prior to intervention occurring. An example of a typical intervention delay may be around thirty seconds to one minute. The notification may be transmitted to the driver by the output control module 216. This notification serves to inform the driver that the impairment value is greater than the operational intervention threshold, and, as a result, operational intervention may occur after the intervention delay expires. The remaining time on the intervention delay may also be displayed in the notification.

After the intervention delay expires, if the ignition state 178 has not been cycled to off or accessary, the intervention module 210 proceeds to activate a plurality of control enhancing features. Some of these features may include at least one traction control, stability control, automatic headlights, lane keep assist, lane departure warning, and full-range adaptive cruise control. These features may be activated by sending activation signals 240 to the corresponding modules using the CAN 162. Another example would be to change the sensitivity of steering response by sending steering control signals 242 to the steering control module 140. Additionally, the vehicle's speed and acceleration could be limited. As an example only, if the operator is driving a sports car, the steering, speed, and acceleration could be limited in such a way that it behaves as a different vehicle, such as an economy sedan or something similar.

The degree of intervention may vary when a cellular transceiver (Tx/Rx) 214 is connected to a cellular network. As a result, the cellular transceiver 214 may continuously attempt to connect to the cellular network while the vehicle is on. The cellular transceiver 214 may generate a cellular connection signal 248 that indicates whether the cellular transceiver 214 is presently connected to the cellular network.

When the cellular transceiver 214 is not connected to the cellular network (indicating that the vehicle is out of range of coverage of the cellular network), the intervention module 210 may send engine commands 228 to limit the vehicle speed to a predetermined maximum speed. The predetermined maximum speed is calibratable, such as 30 mph, 40 mph, 50 mph, 60 mph, or 70 mph. In various implementations, the predetermined maximum speed may be a maximum possible speed of the vehicle as to not limit the speed of the vehicle when the cellular transceiver 214 is not connected to the cellular network. The intervention module 210 may generate the transmission commands 232 to include a command to shift the transmission 110 to neutral.

Additionally, the intervention module 210 may generate audio/visual (A/V) commands 254 to the output control module 216. The output control module 216 may generate external audio/visual control signals 250 and 251 according to the audio/visual commands 254, for example, to warn other drivers of the operator's impairment. As an example, the output control module 216 send control signals 280 to illuminate or flash (on and off) one or more of the exterior lights 194. These external lights 194 may include headlights, high-beam headlights, and hazard lights. The output control module 216 may additionally or alternatively issue control signals 251 to generate sound using the horn 195. In various implementations, the output control module 216 may command the exterior control module 192 to perform these actions.

When the cellular transceiver 214 is connected to the cellular network, the intervention module may send a signal to notify emergency services of the impaired driver. This notification may include the location of the vehicle, whether it is moving or stationary, and the impairment value of the driver.

Emergency services may include at least one of a police department, Emergency Medical Services (EMS), a fire department, and similar emergency response groups. Additionally, these services may include AAA, OnStar, Allstate or any number of companies that offer roadside assistance. In an embodiment where there is access to the contact list of a cellular device connected to the vehicle, the emergency contacts stored in the cellular device may be utilized.

Additionally, if the cellular transceiver 214 is connected to the cellular network, the intervention module 210 may determine if a full vehicle stop is appropriate using parameters such as road data, traffic conditions, location, and weather.

When the cellular transceiver 214 is connected to the cellular network, the intervention module 210 may set the audio/visual commands to first predetermined audio/visual commands. When the cellular transceiver 214 is not connected to the cellular network or when a full vehicle stop is not appropriate, the intervention module 210 may set the audio/visual commands to second predetermined audio/visual commands. The first predetermined audio/visual commands may be externally less obvious than the second predetermined audio/visual commands.

For example, the first predetermined audio/visual commands may include a command to flash the exterior lights 194 on and off at a first predetermined intensity and/or at a first predetermined rate. The first predetermined audio/visual commands may also include a command to honk the horn 195 at a first predetermined duration continuously or on and off at a second predetermined rate. The second predetermined audio/visual commands may include a command to flash the exterior lights 194 on and off at a second predetermined intensity and/or at a second predetermined rate. The second predetermined intensity may be greater than the first predetermined intensity and/or the second predetermined rate may be greater than the first predetermined rate as to be visually more obvious. The first predetermined audio/visual commands may also include a command to turn the horn 195 for a first predetermined duration before turning the horn 195 off or turning the horn 195 on (based on the first predetermined duration) and off at a third predetermined rate. The second predetermined audio/visual commands may also include a command to turn the horn 195 for a second predetermined duration before turning the horn 195 off or turning the horn 195 on (based on the second predetermined duration) and off at a fourth predetermined rate. The fourth predetermined duration may be greater than the third predetermined duration and/or the fourth predetermined rate may be greater than the third predetermined rate as to be audibly more obvious.

The resample calculator module 220 may be used to calculate the amount of time between impairment samples taken by the impairment sample module 204. A sample frequency, representing this time between samples, may be set to a fixed value and remain constant throughout operation, or it may vary depending on several parameters. The resample calculator module 220 receives previous impairment values 222 and uses these values along with additional information to calculate a resample period 224 to control the impairment sample module 204.

One parameter that may be used to calculate the sample frequency is the previous impairment value or values. Using this information, the resample calculator module 220 may determine a longer time between samples if the previous impairment values show a very low level of impairment or no impairment at all. On the contrary, if the warning threshold value was surpassed, the time for the next sample may be relatively short to both confirm that the previous reading was not a false positive and to make sure that the impairment value does not rise to the level of operational intervention. Additionally, the resample calculator module 220 may monitor for trends in the impairment values when calculating the resample frequency. For example, if the impairment values are steadily increasing, the time between samples may need to be shorter to more accurately determine when the threshold values are exceeded, or if the values are steadily decreasing, it may not be critical to sample as frequently.

Using methods such as these to determine a variable sample frequency can be very helpful in extending the life of the system. The resample calculator module 220 may determine that a large time between samples is sufficient, or that no resample is necessary, and this may minimize the number of samples taken. Consequently, the impairment detection devices may last longer without needing replacement or maintenance.

Figure 3:
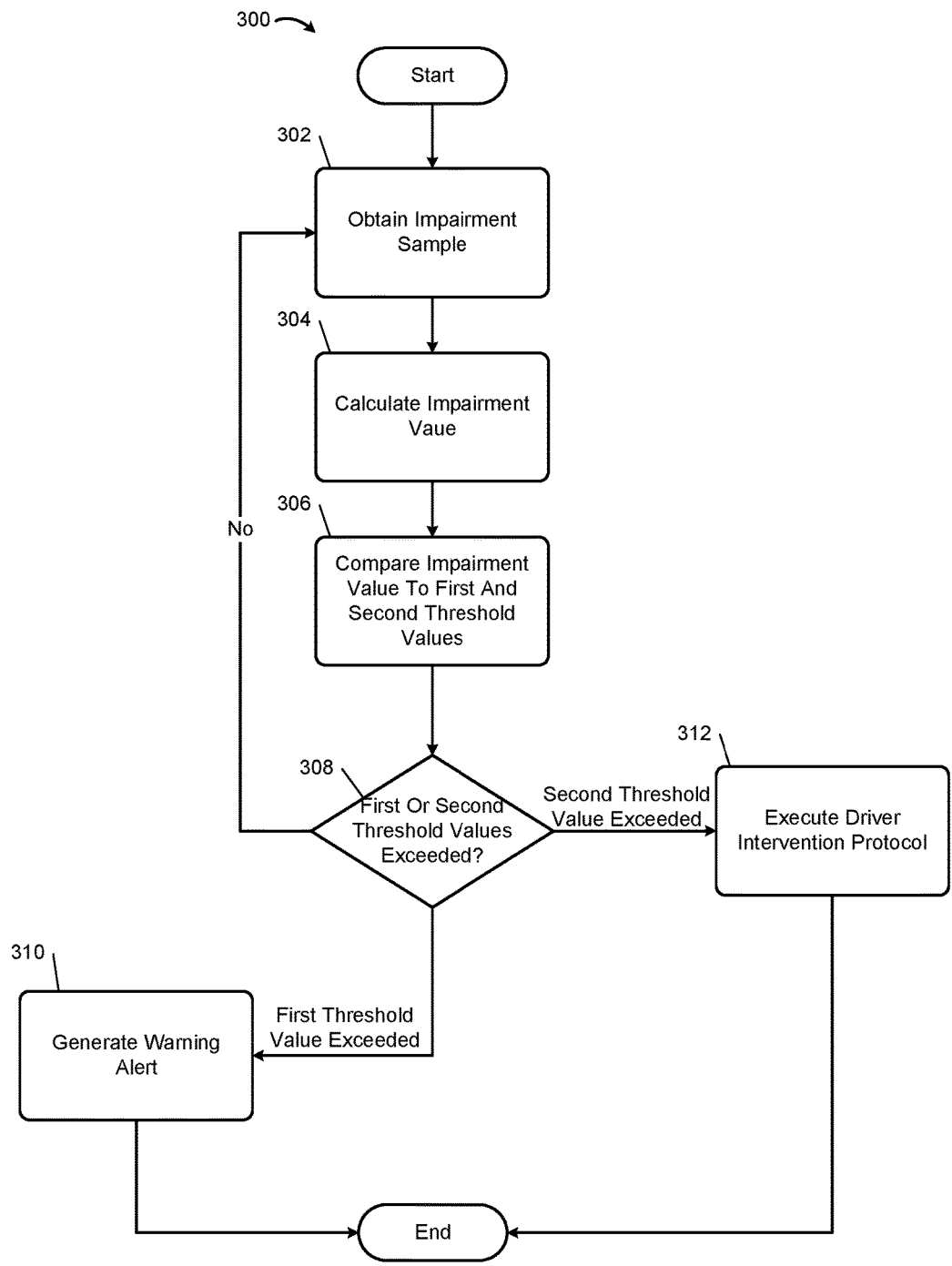
FIG. 3 is a flowchart showing an example method of monitoring operator impairment and performing vehicle control.

FIG. 3 shows an example method 300 for monitoring operator impairment and initiating intervention when impairment levels reach the thresholds.

The method 300 begins at 302 where an impairment sample is obtained. In one embodiment, the impairment measurement device 198 samples the impairment (e.g., BAC) of the driver of the vehicle, and the impairment sample module 204 obtains this sample. This may be initiated by the ignition state 178 transitioning to accessory or crank, for example, by actuating an ignition key, button, or switch.

At 304 an impairment value is calculated for the impairment sample. For example, the impairment value calculator module 206 may calculate an impairment value for the impairment sample, if this was not already done by the impairment measurement device 198. Some devices may be configured to provide samples corresponding to an impairment value; otherwise, this value may be calculated.

At 306, the impairment value is compared with a first and second threshold value. By way of example, the threshold comparison module 208 may determine if the impairment value is greater than either the first (warning) or second (operational intervention) threshold values. If the impairment value is not greater than either the warning threshold value or the operational intervention value, then control returns to 302 to obtain the next impairment sample when initiated by the resample calculator module 220. If the impairment value is greater than the warning threshold but is not greater than the operational intervention threshold, control continues to 310. If the impairment value is greater than the operational intervention value, control continues to 312.

At 310, a warning alert is generated. In one instance, the warning alert module 212 may generate the warning alert. The alert may be transmitted to the driver via the output control module 216. This warning alert may include an alert message displayed on 184 and an audible note played by the speakers 190. This may be initiated by the output control module 216 using control signal 272 to control the display and 276 to control the speakers. Additionally, the warning alert may include visual and/or audible outputs such as controlling the external lights 194 and the horn 195. This may be initiated by the output control module 216 using control signal 250 to control the external lights and 251 to control the horn.

At 312, driver intervention protocol is executed. For example, the intervention module 210 may execute driver intervention protocol. This intervention protocol may begin by initiating the intervention delay that gives the driver time to terminate operation of the vehicle by their own means before operational intervention occurs. Additionally, a message may be transmitted to the driver to inform of the pending intervention. This may be transmitted by the output control module 216 to the display 184. After the intervention delay has expired, control enhancing features may be activated. These feature may include traction control, stability control, automatic headlights, lane keep assist, lane departure warning, and range adaptive cruise control.

Figure 4:
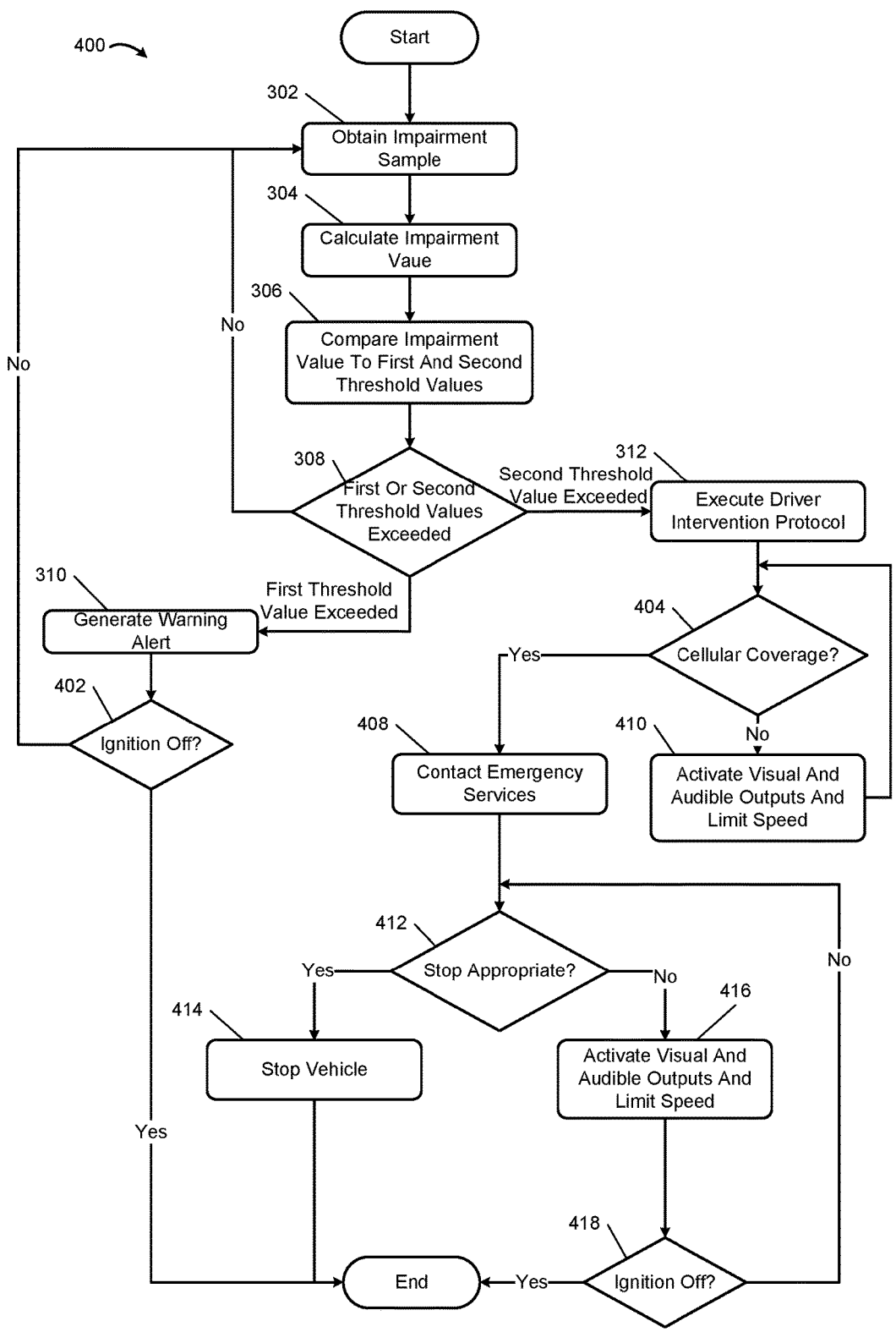
FIG. 4 is a flowchart showing another detailed example method of monitoring operator impairment and performing vehicle control.

FIG. 4 is a flowchart depicting an example detailed method 400 for monitoring operator impairment and performing vehicle intervention. The first steps (302-312) of method 400 are the same as method 300, but further details on what occurs after the initial response to checking if the impairment value exceeds either of the first and second threshold values.

After the system generates a warning alert at 310, the ignition state 178 is checked at 402. If the ignition state 178 is off or accessory, the monitoring cycle ends. However, if the ignition state 178 is not off or accessory, the process continues at 302 by obtaining another impairment sample at the appropriate time issued by the resample control module 220.

After the system executes driver intervention protocol at 312, the cellular coverage is evaluated at 404. For example, the intervention module 210 may receive a cellular connection signal 248 from the cellular receiver 214 which contains whether the cellular receiver 214 is connected to a cellular network.

In one embodiment, when there is no cellular coverage present, the intervention module may not allow the vehicle to be brought to a full stop because there is no way to contact emergency services. Consequently, if cellular service is not present, the invention module 210 may activate visual and audible outputs and limit the speed at 410. These outputs, including the external lights 194 and the horn 195, may be controlled by the output control module 216 which receives control signals from the intervention module 210.

Limiting the speed may include restricting the speed to a specific range. The intervention module 210 may restrict the speed using engine commands 228 to the ECM 106. The ECM 106 selectively limits torque output of the engine 102 based on the engine commands 228. For example, the engine commands 228 may include a maximum vehicle speed. The ECM 106 may limit torque output of the engine 102 to limit a vehicle speed from exceeding the maximum vehicle speed. The speed may be limited to prevent excessive speeds that surpass the speed limits of the road. Additionally, the speed may be limited depending on parameters of the vehicle, road, and current conditions. Some specific parameters that may dictate the speed limits include model of the vehicle, road location, road geography, weather conditions, and traffic conditions.

For example, if the road contained many hills or sharp turns, the speed may be limited to a lower top speed. Another example is if the weather was cold enough for ice to form, the top speed may be set to a lower limit to reduce the risk of loss of control on ice. On the contrary, if the vehicle was entering a highway, there may be a need to set a minimum speed. In this case, the speed of traffic on the highway may be used to determine this minimum speed. After this has been completed, the process returns to step 404 to continue to monitor for the presence of cellular service.

If at 404 it is determined that cellular coverage is present, emergency services are contacted at 408. This may include informing emergency services that the driver is impaired, the impairment value of the driver, and the location of the vehicle (moving or stationary). If the impairment value is high enough, it may be determined that the operator needs medical attention. In which case, specific response services may be required.

At 412, it is determined if a full stop is appropriate. In one embodiment, the intervention module 210 may determine if a full vehicle stop is appropriate. In order to determine this, many parameters may be considered. As an example, the location of the vehicle may be considered. This information may include road data, such as if there is a shoulder on the side of the road. If there is no shoulder in which the vehicle may stop, it may not be appropriate to bring the vehicle to a full stop. If the vehicle is on a bridge with limited space, a full stop may not be appropriate. Other information may include the heading of the vehicle. If the vehicle was in the middle of oncoming traffic, it may not be appropriate to initiate a full stop without first navigating the vehicle to the appropriate side of the road. Weather and visibility conditions may be considered. If the visibility is very limited, making it difficult for other drivers to see the stopped vehicle, it may not be appropriate to stop the vehicle. Similarly, if the road conditions are extremely slick due to ice, rain or something similar and other drivers may not be able to avoid the stopped vehicle, a full stop may not be appropriate.

If it is determined that a full stop is appropriate at 412, the vehicle is brought to a stop at 414. This step may include changing the ignition state 178 to off or accessory and ending the impairment monitoring, or it may include allowing the vehicle to remain running but not allowing the vehicle to move or the transmission to be shifted out of park. In that case, the impairment monitoring may continue, and when the impairment value is below the operational intervention threshold, the operator may be allowed to resume control of the vehicle.

If it is determined that a full stop is not appropriate at 412, visual and audible outputs are activated and the speed limited at 416. As an example, this may be initiated by the intervention module 210 and use the output control module 216. These measures could be similar or identical to the measures taken in step 410.

After the measures at 416 have been activated, if the ignition state 178 is off or accessory, the monitoring ends, but if the ignition state 178 is not off or accessory, the method returns to 412 to continue to check if a full stop is appropriate.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A drive-cycle sampling and monitoring system comprising:
    an impairment sample module configured to obtain a first impairment sample for an operator of a vehicle while the vehicle is running;
    an impairment value calculator module configured to calculate a first impairment value based on the first impairment sample;
    a threshold comparison module configured to compare the first impairment value to a first threshold value corresponding to a first range of impairment and a second threshold value corresponding to a second range of impairment, wherein the second range of impairment is greater than the first range of impairment;
    a warning alert module configured to generate a warning alert in response to determining that the first impairment value exceeds the first threshold value;
    a cellular transceiver configured to determine if the cellular transceiver is connected to a cellular network; and
    an intervention module configured to execute driver intervention protocol in response to determining that the first impairment value exceeds the second threshold value,
    wherein the driver intervention protocol includes preventing the vehicle from exceeding a maximum vehicle speed when the cellular transceiver is not connected to the cellular network.

2. The system of claim 1, wherein the intervention module is configured to perform at least one of:
    generate an intervention alert; and
    control the operation of the vehicle.

3. The system of claim 2, wherein the intervention alert comprises at least one of a driver warning alert and a notice of pending vehicle intervention.

4. The system of claim 2, wherein the intervention module is configured to control the operation of the vehicle through at least one of:
    wait for an intervention delay to expire;
    adjust a steering response of the vehicle;
    adjust a speed of the vehicle; and
    adjust an acceleration of the vehicle.

5. The system of claim 2, wherein the intervention module is configured to control operation of the vehicle by enabling at least one of traction control, stability control, lane keep assist, and full-range adaptive cruise control.

6. The system of claim 2, wherein the intervention module is configured to:
    if cellular coverage is present, notify emergency services; and
    if cellular coverage is not present, activate a plurality of visual and audible annunciators including at least one of hazard flashers, high-beam headlights, and a horn.

7. The system of claim 1, wherein the intervention module is configured to:
in response to the presence of cellular coverage, determine if a full vehicle stop is appropriate;
if the full vehicle stop is appropriate, stop the vehicle; and
if the full vehicle stop is not appropriate, setting speed limits for the vehicle and activating at least one of the plurality of visual and audible annunciators.

8. The system of claim 1, wherein the warning alert module is configured to perform at least one of:
generate an advisory alert; and
activate visual annunciators, including at least one of hazard flashers and high-beam headlights.

9. The system of claim 1, further comprising an output control module configured to transmit control signals to at least one of a speaker, a horn, a display, and external lights.

10. The system of claim 1 wherein:
the impairment sample module is configured to obtain a second impairment sample for the operator of the vehicle while the vehicle is running;
the impairment value calculator module is configured to calculate a second impairment value based on the second impairment sample;
the threshold comparison module is configured to compare the second impairment value to the first threshold value corresponding to the first range of impairment and the second threshold value corresponding to the second range of impairment, wherein the second range of impairment is greater than the first range of impairment;
the warning alert module is configured to generate a warning alert in response to determining that the second impairment value exceeds the first threshold value; and
the intervention module is configured to execute driver intervention protocol in response to determining that the second impairment value exceeds the second threshold value.

11. The system of claim 10, further comprising a resample calculator module configured to obtain the second impairment sample a predetermined period of time after obtaining the first impairment sample, wherein the predetermined period of time is based on the first impairment value.

12. A method for drive-cycle sampling and monitoring for operator impairment, the method comprising:
obtaining a first impairment sample for an operator of a vehicle while the vehicle is running;
calculating a first impairment value based on the first impairment sample; and
comparing the first impairment value to a first threshold value corresponding to a first range of impairment and a second threshold value corresponding to a second range of impairment, wherein the second range of impairment is greater than the first range of impairment;
in response to detecting the first impairment value exceeds the second threshold value and cellular coverage is not present, executing a driver intervention protocol that includes preventing the vehicle from exceeding a maximum vehicle speed.

13. The method of claim 12, wherein executing the driver intervention protocol further comprises at least one of generating an intervention alert and controlling operation of the vehicle.

14. The method of claim 13, wherein generating an intervention alert comprises at least one of generating a driver warning alert and generating a notice of pending vehicle intervention.

15. The method of claim 13, wherein controlling operation of the vehicle comprises at least one of waiting for an intervention delay to expire, adjusting a steering response of the vehicle, adjusting a speed of the vehicle, adjusting an acceleration of the vehicle, and enabling at least one of traction control, stability control, lane keep assist, and full-range adaptive cruise control.

16. The method of claim 13, wherein in response to detecting the first impairment value exceeds the second threshold value and cellular coverage is present, notifying emergency services.

17. The method of claim 16, further comprising, in response to detecting the first impairment value exceeds at least one of the first threshold value and the second threshold value and cellular coverage is present, stopping the vehicle.

18. The method of claim 13, wherein controlling the operation of the vehicle further comprises:
in response to detecting the first impairment value exceeds at least one of the first threshold value and the second threshold value and cellular coverage is not present, activating a plurality of visual and audible annunciators including at least one of activating hazard flashers, flashing high-beam headlights, and honking vehicle horn.

19. The method of claim 12, wherein generating a warning alert comprises at least one of generating an advisory alert and activating visual annunciators, including at least one of hazard flashers and high-beam headlights.

20. The method of claim 12, further comprising:
obtaining a second impairment sample for the operator of the vehicle, while the vehicle is running, a predetermined period of time after obtaining the first impairment sample, wherein the predetermined period of time is based on the first impairment value;
calculating a second impairment value based on the second impairment sample; and
in response to detecting the second impairment value exceeds the first threshold value, generating a warning alert.

21. The method of claim 12, further comprising:
obtaining a second impairment sample for the operator of the vehicle, while the vehicle is running, a predetermined period of time after obtaining the first impairment sample, wherein the predetermined period of time is based on the first impairment value;
calculating a second impairment value based on the second impairment sample, wherein the second range of impairment is greater than the first range of impairment; and
in response to detecting that the second impairment value exceeds the second threshold value, executing the driver intervention protocol.

22. The method of claim 12, further comprising generating a warning alert in response to detecting the first impairment value exceeds the first threshold value.

* * * * *